United States Patent
Powell et al.

(10) Patent No.: US 10,167,243 B2
(45) Date of Patent: Jan. 1, 2019

(54) BIOMASS CONVERSION PROCESS TO HYDROCARBONS

(71) Applicant: SHELL OIL COMPANY, Houston, TX (US)

(72) Inventors: Joseph Broun Powell, Houston, TX (US); Kimberly Ann Johnson, Richmond, TX (US)

(73) Assignee: SHELL OIL COMPANY, Houston, TX (US)

( * ) Notice: Subject to any disclaimer, the term of this patent is extended or adjusted under 35 U.S.C. 154(b) by 22 days.

(21) Appl. No.: 15/194,650

(22) Filed: Jun. 28, 2016

(65) Prior Publication Data

US 2017/0001934 A1    Jan. 5, 2017

Related U.S. Application Data

(60) Provisional application No. 62/186,919, filed on Jun. 30, 2015.

(51) Int. Cl.
| | |
|---|---|
| *C10G 1/06* | (2006.01) |
| *C10G 3/00* | (2006.01) |
| *C10L 1/04* | (2006.01) |
| *C07C 29/60* | (2006.01) |

(52) U.S. Cl.
CPC ............... *C07C 29/60* (2013.01); *C10G 3/42* (2013.01); *C10G 3/44* (2013.01); *C10G 3/48* (2013.01); *C10G 3/49* (2013.01); *C10G 3/50* (2013.01); *C10G 2300/1014* (2013.01);
(Continued)

(58) Field of Classification Search
CPC .. C07C 29/60; C10G 3/49; C10G 3/48; C10G 2300/202; C10G 2400/30; C10G 2400/22
See application file for complete search history.

(56) References Cited

U.S. PATENT DOCUMENTS

| | | | |
|---|---|---|---|
| 4,717,708 A | * | 1/1988 | Cheng ................. B01J 35/1047 502/233 |
| 8,143,464 B2 | | 3/2012 | Cheiky et al. |

(Continued)

OTHER PUBLICATIONS

Tanneru et al. (Production of transportation fuels range hydrocarbons from pyrolysis oil via a low hydrogen catalytic deoxygenation, 2013 AICHE Annual Meeting) (Year: 2013).*

(Continued)

*Primary Examiner* — Youngsul Jeong (57) ABSTRACT

An improved process for the production of a higher hydrocarbon from solid biomass is provided. Solid biomass that has been digested and hydrodeoxygenated in a liquid digestive solvent in the presence of a hydrothermal hydrocatalytic catalyst is separated to an organic rich phase and an aqueous rich phase containing diols. At least a portion of the aqueous rich phase is contacted with an acidic amorphous silica alumina catalyst producing monooxygenate-containing stream comprising water, organic monooxygenates, and unsaturated aliphatic hydrocarbons. At least a portion of the monooxygenate-containing stream is contacted with a solid acid condensation catalyst to produce a higher hydrocarbons stream. At least a portion of the organic rich phase is also contacted with a solid acid condensation catalyst to produce a higher hydrocarbons stream.

24 Claims, 3 Drawing Sheets

(52) U.S. Cl.
CPC ... *C10G 2300/202* (2013.01); *C10G 2400/22* (2013.01); *C10G 2400/30* (2013.01); *Y02P 30/20* (2015.11)

(56) References Cited

U.S. PATENT DOCUMENTS

| | | | |
|---|---|---|---|
| 8,350,108 B2 * | 1/2013 | Cortright | B01J 23/6567 585/331 |
| 9,347,178 B2 | 5/2016 | Powell et al. | |
| 9,353,478 B2 | 5/2016 | Powell et al. | |
| 2008/0300435 A1 | 12/2008 | Cortright | |
| 2010/0236988 A1 | 9/2010 | Gabrielov | |
| 2012/0317872 A1 | 12/2012 | Powell et al. | |
| 2013/0109896 A1 | 5/2013 | Powell et al. | |
| 2013/0152457 A1 | 6/2013 | Powell et al. | |
| 2013/0152458 A1 | 6/2013 | Powell et al. | |
| 2014/0005444 A1 * | 1/2014 | Komplin | C07C 29/132 568/861 |
| 2014/0005445 A1 | 1/2014 | Komplin et al. | |
| 2014/0117275 A1 | 5/2014 | Powell et al. | |
| 2014/0117276 A1 | 5/2014 | Powell et al. | |
| 2014/0117277 A1 | 5/2014 | Powell et al. | |
| 2014/0121418 A1 | 5/2014 | Powell et al. | |
| 2014/0121419 A1 | 5/2014 | Powell et al. | |
| 2014/0128639 A1 | 5/2014 | Powell et al. | |
| 2014/0166221 A1 | 6/2014 | Powell et al. | |
| 2014/0174432 A1 | 6/2014 | Powell et al. | |
| 2014/0174433 A1 * | 6/2014 | Powell | B01J 8/22 127/1 |
| 2014/0275515 A1 | 9/2014 | Powell et al. | |
| 2015/0166681 A1 | 6/2015 | Chheda et al. | |
| 2015/0166682 A1 | 6/2015 | Powell et al. | |
| 2015/0167235 A1 | 6/2015 | Powell et al. | |
| 2015/0167238 A1 | 6/2015 | Powell et al. | |
| 2015/0167239 A1 | 6/2015 | Powell et al. | |
| 2015/0167240 A1 | 6/2015 | Powell et al. | |
| 2015/0167241 A1 | 6/2015 | Powell et al. | |
| 2015/0184081 A1 | 7/2015 | Powell et al. | |

OTHER PUBLICATIONS

Mullern et al. (Production of deoxygenated biomass fast pyrolysis oils via product gas recycling, Energy and Fuels, 2013, vol. 27, pp. 3867-3874) (Year: 2013).*

International Search Report and Written Opinion received for PCT Patent Application No. PCT/US2016/039742, dated Oct. 14, 2016, 9 pages.

Topspe. et al., "Hydrotreating Catalysis", Catalysis Science and Technology, 1996, vol. 11, Chapter 2, pp. 12-24, Springer-Verlag Publishers, Heidelberg.

* cited by examiner

BIOMASS CONVERSION PROCESS TO HYDROCARBONS

The present application claims the benefit of U.S. Provisional Application Ser. No. 62/186,919, filed 30 Jun. 2015, the entire disclosure of which is hereby incorporated by reference.

FIELD OF THE INVENTION

The invention relates to conversion of biomass to hydrocarbons. More specifically, the invention relates to improved production of higher hydrocarbons useful as liquid biofuels from solid biomass.

BACKGROUND OF THE INVENTION

A significant amount of attention has been placed on developing new technologies for providing energy from resources other than fossil fuels. Biomass is a resource that shows promise as a fossil fuel alternative. As opposed to fossil fuel, biomass is also renewable.

Biomass may be useful as a source of renewable fuels. One type of biomass is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose. Hemicellulose and pectin are typically found in abundance, but cellulose is the predominant polysaccharide and the most abundant source of carbohydrates. However, production of fuel from cellulose poses a difficult technical problem. Some of the factors for this difficulty are the physical density of lignocelluloses (like wood) that can make penetration of the biomass structure of lignocelluloses with chemicals difficult and the chemical complexity of lignocelluloses that lead to difficulty in breaking down the long chain polymeric structure of cellulose into carbohydrates that can be used to produce fuel. Another factor for this difficulty is the nitrogen compounds and sulfur compounds contained in the biomass. The nitrogen and sulfur compounds contained in the biomass can poison catalysts used in subsequent processing.

Most transportation vehicles require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier.

Currently, bio-based feedstocks such as biomass provide the only renewable alternative for liquid transportation fuel. Unfortunately, the progress in developing new technologies for producing liquid biofuels has been slow in developing, especially for liquid fuel products that fit within the current infrastructure. Although a variety of fuels can be produced from biomass resources, such as ethanol, methanol, and vegetable oil, and gaseous fuels, such as hydrogen and methane, these fuels require either new distribution technologies and/or combustion technologies appropriate for their characteristics. The production of some of these fuels also tends to be expensive and raise questions with respect to their net carbon savings. There is a need to directly process biomass into liquid fuels, amenable to existing infrastructure.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). Further, it is a challenge to minimize generation of waste products that may require treating before disposal and/or catalyst deactivation by poisons.

SUMMARY OF THE INVENTION

It was found that glycols in the oxygenated hydrocarbon intermediate produced by digesting and hydrodeoxygenating solid biomass in a liquid digestive solvent tend to rapidly coke the condensation catalyst in the subsequent condensation reaction that produces higher hydrocarbons. Further, applicants have found that when digestion and hydrodeoxygenation product is allowed to separate into organic-rich and aqueous rich phases, (prior to condensation reaction), oxygenates such as glycols or diols and other water miscible organic compounds such as monooxygenates are lost to the aqueous phase, resulting in loss in yields from the biomass in the production of higher hydrocarbons. Applicants have found that by contacting aqueous phase, which has optionally been enriched in organics, with an acidic amorphous silica alumina catalyst under certain reaction conditions producing monooxygenated stream produces oxygenated product stream (optionally containing unsaturated condensation products such as olefins) resulting in improved product yield.

In one embodiment, a process for the production of a higher hydrocarbon from solid biomass is provided, said process comprising:
a. providing a biomass solid containing cellulose, hemicellulose, and lignin;
b. digesting and hydrodeoxygenating the biomass solid in a liquid digestive solvent in the presence of a hydrothermal hydrocatalytic catalyst and hydrogen at a temperature in the range of 110° C. to less than 300° C. and at a pressure in a range of from 20 bar to 200 bar, said digestive solvent containing a solvent mixture having a boiling point of at least 40° C., to form a stable oxygenated hydrocarbon intermediate product having a viscosity of less than 100 centipoise (at 50° C.), a diol content of at least 2 wt. %, less than 2 wt. % of sugar, and less than 2 wt. % acid (based on acetic acid equivalent), based on the intermediate product, and at least 60% of carbon exists in molecules having 9 carbon atoms or less;
c. separating the stable oxygenated hydrocarbon intermediate product to an organic rich phase and an aqueous rich phase;
d. reacting at least a portion of the aqueous rich phase with an acidic amorphous silica alumina catalyst at a temperature in the range from 300° C. to 400° C. thereby producing monooxygenate-containing stream comprising water, organic monooxygenates, and unsaturated aliphatic hydrocarbons;
e. contacting at least a portion of the monooxygenate-containing stream with solid acid condensation catalyst at a temperature in the range from 275° C. to about 425° C. producing a higher hydrocarbons stream; and
f. contacting at least a portion of the organic rich phase with solid acid condensation catalyst at a temperature in the range from 275° C. to about 425° C. producing a higher hydrocarbons stream.

In another embodiment, a process for the production of a higher hydrocarbon from solid biomass is provided, said process comprising:
a. providing a biomass solid containing cellulose, hemicellulose, and lignin;
b. digesting and hydrodeoxygenating the biomass solid in a liquid digestive solvent in the presence of a hydrothermal hydrocatalytic catalyst and hydrogen at a temperature in the range of 110° C. to less than 300° C. and at a pressure in a range of from 20 bar to 200 bar, said digestive solvent containing a solvent mixture having a boiling point of at least 40° C., to form a stable oxygenated hydrocarbon intermediate product having a viscosity of less than 100 centipoise (at 50° C.), a diol content of at least 2 wt. %, less than 2 wt. % of sugar, and less than 2 wt. % acid (based on acetic acid equivalent), based on the intermediate product, and at least 60% of carbon exists in molecules having 9 carbon atoms or less;
c1. adding an aromatics-rich higher hydrocarbon comprising toluene to the stable oxygenated hydrocarbon intermediate product providing an toluene-added stable oxygenated hydrocarbon intermediate.
c2. separating the toluene-added stable oxygenated hydrocarbon intermediate to an organic rich phase and an aqueous rich phase;
d. reacting at least a portion of the aqueous rich phase with an acidic amorphous silica alumina catalyst at a temperature in the range from 300° C. to 400° C. thereby producing monooxygenate-containing stream containing water and organic monooxygenates;
e. contacting at least a portion of the organic monooxygenate-containing stream with an acidic ZSM-5 catalyst at a temperature in the range from 325° C. to about 425° C. producing water and an aromatics-rich higher hydrocarbons stream comprising toluene;
f. contacting at least a portion of the organic rich phase with solid acid condensation catalyst at a temperature in the range from 275° C. to about 425° C. producing a higher hydrocarbons stream; and
g. recycling at least a portion of the aromatics-rich higher hydrocarbons stream comprising toluene to step (c1) as a portion of the aromatics-rich higher hydrocarbon.

The condensation reactions may be in the same reactor or different reactors.

The features and advantages of the invention will be apparent to those skilled in the art. While numerous changes may be made by those skilled in the art, such changes are within the spirit of the invention.

BRIEF DESCRIPTION OF THE DRAWING

The drawings illustrate certain aspects of some of the embodiments of the invention, and should not be used to limit or define the invention.

DETAILED DESCRIPTION OF THE INVENTION

In one embodiment, the invention relates to contacting the aqueous phase from the reaction products, produced from digesting and hydrodeoxygenating a solid biomass in a liquid digestive solvent, with an acidic amorphous silica alumina catalyst under certain reaction conditions producing monooxygenated stream that can also be subjected to condensation reaction to produce higher hydrocarbons. Applicants have found that glycols in the oxygenated hydrocarbon intermediate produced by digesting and hydrodeoxygenating solid biomass in a liquid digestive solvent tend to rapidly coke the condensation catalyst in the subsequent condensation reaction that produces higher hydrocarbons. Further, applicants have found that when digestion and hydrodeoxygenation product is allowed to separate into organic-rich and aqueous rich phases, (prior to condensation reaction), oxygenates such as glycols or diols and other water miscible organic compounds such as monooxygenates is lost to the aqueous phase, resulting in loss in yields from the biomass in the production of higher hydrocarbons. Applicants have found that by contacting aqueous phase, which has optionally been enriched in organics, with an acidic amorphous silica alumina catalyst under certain reaction conditions producing monooxygenated stream produces oxygenated product stream (optionally containing unsaturated condensation products such as olefins) resulting in improved product yield.

The higher hydrocarbons produced are useful in forming transportation fuels, such as synthetic gasoline. As used herein, the term "higher hydrocarbons" refers to hydrocarbons having an oxygen to carbon ratio less than the oxygen to carbon ratio of at least one component of the biomass feedstock. The higher hydrocarbon predominantly contains C4 to C30 hydrocarbons, more preferably C6 to C18 hydrocarbons. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (i.e., oxygen sulfur, phosphorus, or nitrogen) and thus the term "hydrocarbon" may also include substituted hydrocarbons. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. Further the process should maximize product yield while minimizing waste products. These basic requirements lead to a number of secondary issues that collectively present an immense engineering challenge that has not been solved heretofore.

In a method of production of hydrocarbons, pyrolysis of biomass has been reported. Pyrolysis is the thermal decomposition of biomass occurring in the absence of oxygen. The products of biomass pyrolysis include biochar, bio-oil and gases including methane, hydrogen, carbon monoxide, and carbon dioxide. Depending on the thermal environment and the final temperature, pyrolysis will yield mainly biochar at low temperatures, less than 450° C., when the heating rate is quite slow, and mainly gases at high temperatures, greater than 800° C., with rapid heating rates. At an intermediate temperature and under relatively high heating rates, the main product is bio-oil. Pyrolysis products can be upgraded to fuel such as disclosed in U.S. Pat. No. 8,143,464. However, such process produces a large quantity of biochar and gases such as methane, hydrogen, carbon monoxide, and carbon dioxide.

Unlike a pyrolysis process, digestion and hydrocatalytic hydrodeoxygenation produces a liquid oxygenated hydrocarbon intermediate with minimal biochar or gaseous carbon monoxide and carbon dioxides. However, under the milder conditions that produces the oxygenated hydrocarbon intermediates also forms glycols that tends to coke the condensation catalyst to produce the higher hydrocarbons.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). It was found that glycols in the oxygenated hydrocarbon intermediate produced by digesting and catalytically hydrodeoxygenating solid biomass in a liquid digestive solvent tend to rapidly coke the condensation catalyst in the subsequent condensation reaction that produces higher hydrocarbons. It was found that contacting (and reacting) the oxygenated hydrocarbon intermediate containing diols with an acidic amorphous silica alumina catalyst at a temperature in the range of 300° C. to 400° C. producing monooxygenated stream prior to condensation reaction can reduce coke formation on the catalyst during condensation reaction.

Optionally, it has further been found that when the monooxygenated stream is condensed, water can be effectively removed from the process by phase separation, further protecting the condensation catalyst from degradation. Upon condensation, the monooxygenated stream readily separates into an aqueous phase containing water and an organic phase containing the monooxygenates. Optionally, at least a portion of the organic phase can be recycled to be used as digestive solvent.

Figure 1:
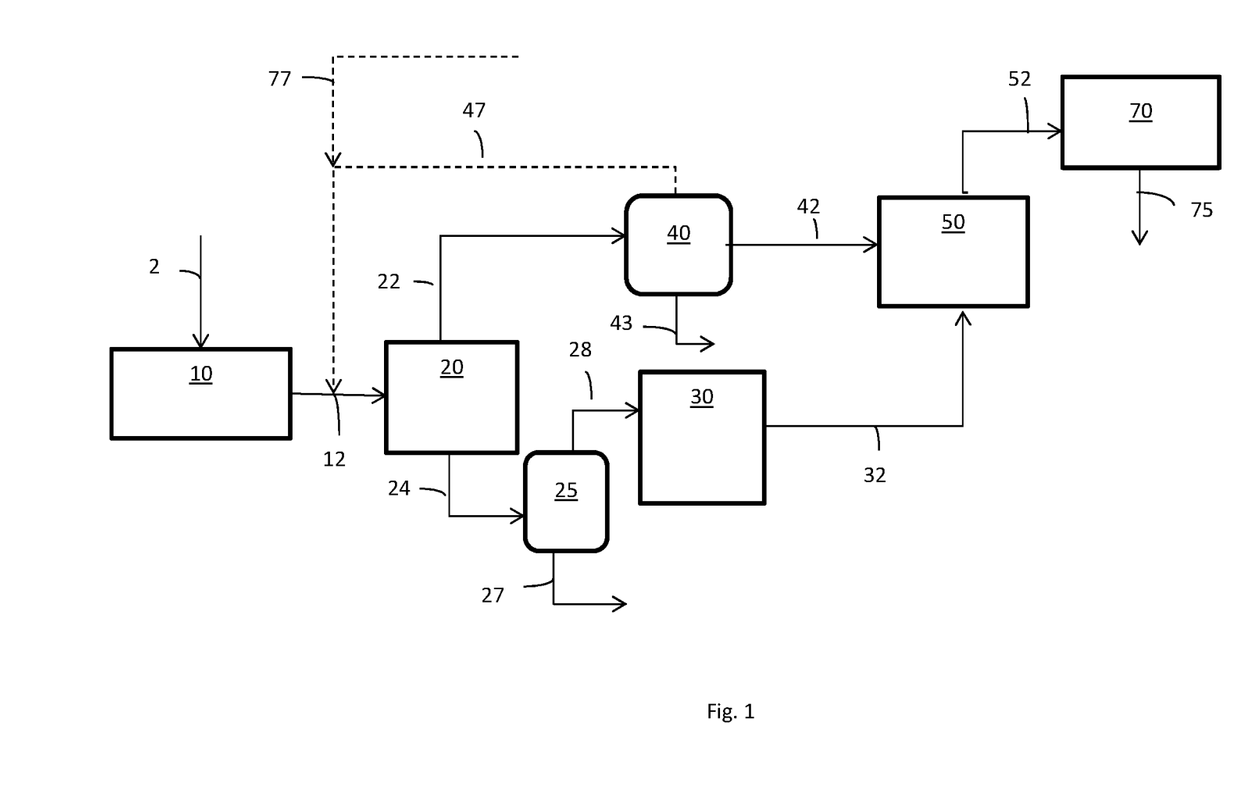
FIG. 1 is a schematic illustration of an embodiment of a process of this invention.
Figure 2:
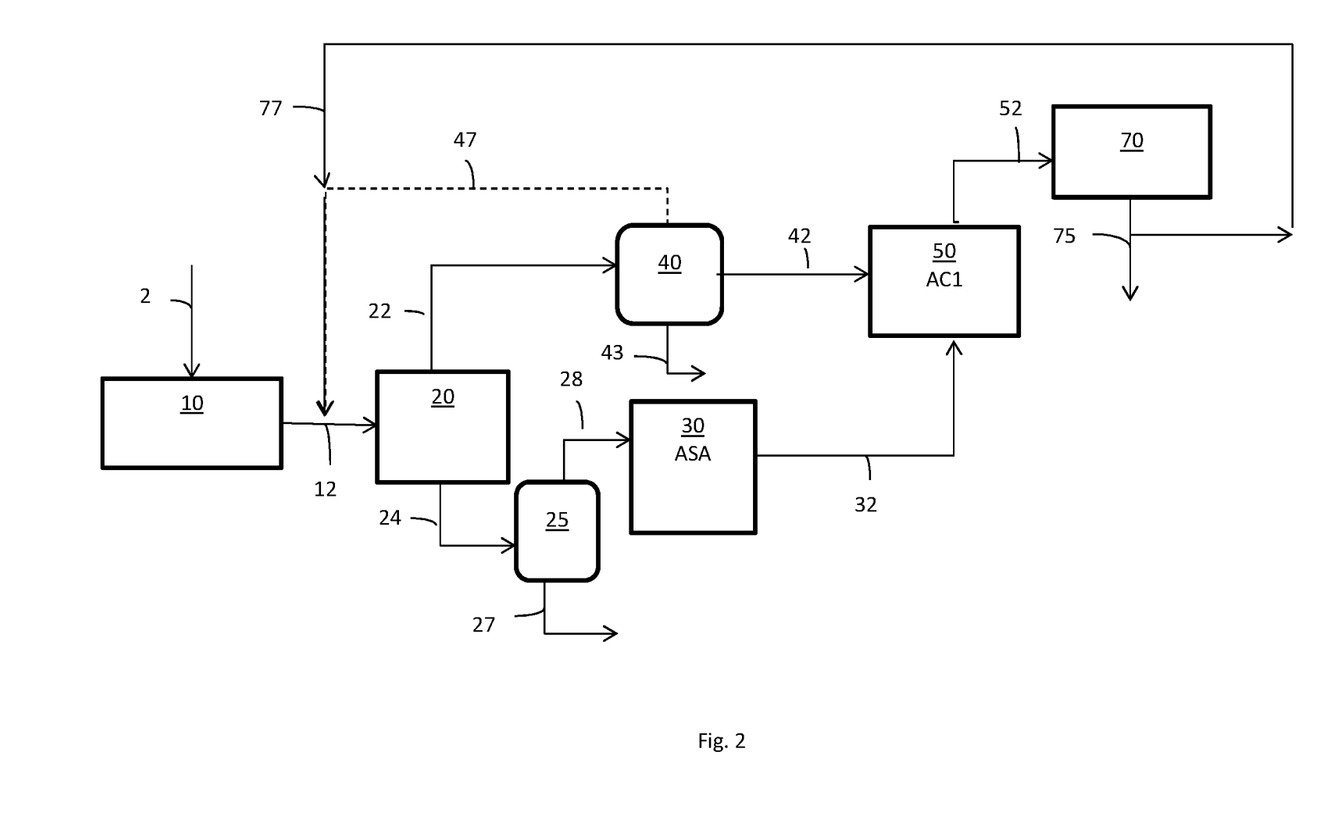
FIG. 2 is a schematic illustration of another embodiment of a process of this invention.
Figure 3:
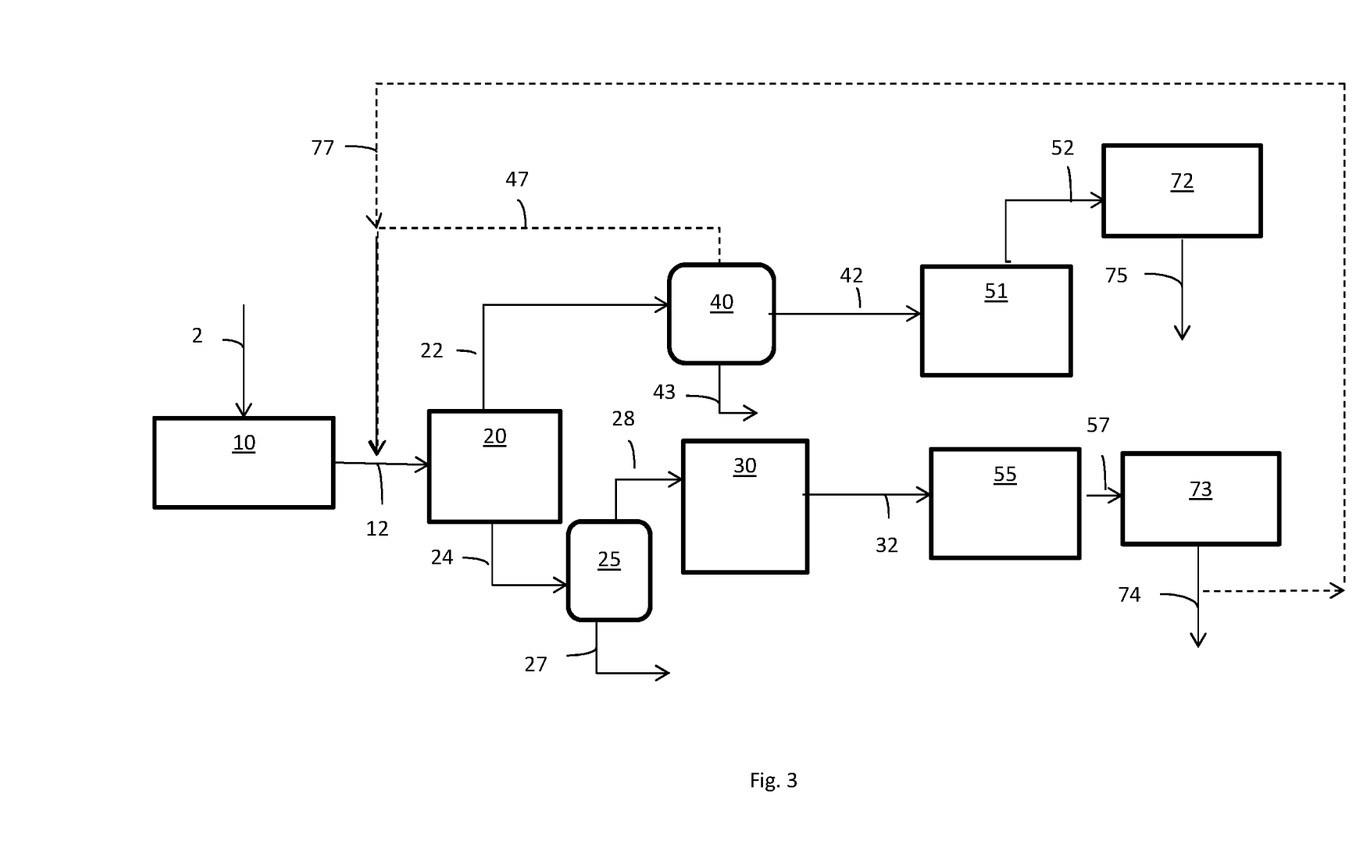
FIG. 3 is a schematic illustration of another embodiment of a process of this invention.

Various illustrative embodiments will be further described with reference to FIG. 1, FIG. 2 and FIG. 3 In FIG. 1, FIG. 2, and FIG. 3 show illustrative embodiments of biomass conversion process to hydrocarbon.

Any suitable (e.g., inexpensive and/or readily available) type of lignocellulosic biomass can be used as a solid biomass. Suitable lignocellulosic biomass can be, for example, selected from, but not limited to, wood, forestry residues, agricultural residues, herbaceous material, municipal solid wastes, pulp and paper mill residues, and combinations thereof. Thus, in some embodiments, the biomass can comprise, for example, corn stover, straw, bagasse, miscanthus, sorghum residue, switch grass, duckweed, bamboo, water hyacinth, hardwood, hardwood chips, hardwood pulp, softwood, softwood chips, softwood pulp, and/or combination of these feedstocks. The biomass can be chosen based upon a consideration such as, but not limited to, cellulose and/or hemicelluloses content, lignin content, growing time/season, growing location/transportation cost, growing costs, harvesting costs and the like.

Prior to processing, the untreated biomass can be reduced in size (e.g., chopping, crushing or debarking) to a convenient size and certain quality that aids in moving the biomass or mixing and impregnating the chemicals from digestive solvent. Thus, in some embodiments, providing biomass can comprise harvesting a lignocelluloses-containing plant such as, for example, a hardwood or softwood tree. The tree can be subjected to debarking, chopping to wood chips of desirable thickness, and washing to remove any residual soil, dirt and the like.

The biomass solids is introduced in to a vessel from an inlet. The vessel can be in any shape that include, for example, vertical, horizontal, incline, and may include bends, curves or u shape. The vessel will further have at least one inlet and at least one outlet.

The biomass may optionally be washed with an acidic or basic solution to remove metal species and its corresponding anions such as Mg, Ca, Na, K Fe, Mn, Cl, $SO_4$, $PO_4$, $NO_3$ that are detrimental to catalysts or equipment used in the hydrothermal hydrocatalytic treatment from the biomass. Such treatment disclosed in commonly owned U.S. Patent Application Nos. 61/917,382, 61/917,400, 61/917,406, 61/917,414, 61/917,393, 61/917,402, 61/917,419, 61/917,422, 61/917,445, and 61/917,448 filed Dec. 18, 2013, which disclosures are hereby incorporated by reference in its entirety.

At least a portion of the optionally treated cellulosic biomass solids is provided to a digestion and/or reaction zone (collectively referred to as "hydrothermal hydrocatalytic reaction zone", 10) for digesting and hydrodeoxygenating. This zone may be conducted in a single step or in multiple steps or vessels as described below.

For the hydrothermal hydrocatalytic reaction zone, the zone may have one or more vessels. In one embodiment in the digestion/reaction zone hydrolysis and hydrothermal hydrocatalytic reaction of the treated biomass is carried out in one or more vessels. These vessels may be digesters or reactors or combination thereof including a combination hydrothermal hydrocatalytic digestion unit.

In some embodiments, lignocellulosic biomass (solids), 2, being continuously or semi-continuously added to the hydrothermal digestion unit or hydrothermal hydrocatalytic digestion unit may be pressurized before being added to the unit, particularly when the hydrothermal (hydrocatalytic) digestion unit is in a pressurized state. Pressurization of the cellulosic biomass solids from atmospheric pressure to a pressurized state may take place in one or more pressurization zones before addition of the cellulosic biomass solids to the hydrothermal (hydrocatalytic) digestion unit. Suitable pressurization zones that may be used for pressurizing and introducing lignocellulosic biomass to a pressurized hydrothermal digestion unit or hydrothermal hydrocatalytic digestion unit are described in more detail in commonly owned U.S. Patent Application Publication Nos. US20130152457 and US20130152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner. The digestion and the hydrothermal hydrocatalytic reaction in the hydrothermal catalytic reaction zone (or digestion reaction zone) may be conducted separately, partially combined, or in situ.

The biomass solid is hydrothermally digested and hydrodeoxygenated in a liquid-phase digestive solvent, in the presence of hydrogen and a catalyst capable of activating molecular hydrogen (hydrothermal hydrocatalytic catalyst), at a temperature in the range of from 110° C. to less than 300° C. at a pressure in a range of from 20 bar to 200 bar to form stable oxygenated hydrocarbon intermediate product mixtures. The stable oxygenated hydrocarbon intermediate product mixture, in general, has a viscosity of less than 100 centipoise (at 50° C.), a glycol content of at least 2 wt. % of diols, less than 2 wt. % of sugar, and less than 2 wt. % organic acid based on acetic acid equivalent, and at least 60% of carbon in formed product exists in molecules having 10 carbon atoms or less. Reference herein to pressure(s) is to gauge pressure(s).

In some embodiments, the digestion rate of cellulosic biomass solids may be accelerated in the presence of a liquid phase containing a digestion solvent. In some instances, the liquid phase may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures. One approach for addressing the degradation of soluble carbohydrates during hydrothermal digestion is to conduct an in situ catalytic reduction reaction process so as to convert the soluble carbohydrates into more stable compounds as soon as possible after their formation.

In certain embodiments, a slurry catalyst may be effectively distributed from the bottom of a charge of cellulosic biomass solids to the top using upwardly directed fluid flow to fluidize and upwardly convey slurry catalyst particulates into the interstitial spaces within the charge for adequate catalyst distribution within the digesting cellulosic biomass solids. Suitable techniques for using fluid flow to distribute a slurry catalyst within cellulosic biomass solids in such a manner are described in commonly owned U.S. Patent Application Publication Nos. US20140005445 and US20140005444, which are incorporated herein by reference in its entirety. In addition to affecting distribution of the slurry catalyst, upwardly directed fluid flow may promote expansion of the cellulosic biomass solids and disfavor gravity-induced compaction that occurs during their addition and digestion, particularly as the digestion process proceeds and their structural integrity decreases. Methods of effectively distributing molecular hydrogen within cellulosic biomass solids during hydrothermal digestion is further described in commonly owned U.S. Patent Application Publication Nos. US20140174433 and US20140174432, which are incorporated herein by reference in its entirety.

In another embodiment the hydrothermal hydrocatalytic digestion unit may be configured as disclosed in a copending U.S. Application Publication No. US20140117276 which disclosure is hereby incorporated by reference. In the digestion zone, the size-reduced biomass is contacted with the digestive solvent where the digestion reaction takes place. The digestive solvent must be effective to digest lignins. The digestive solvent is typically a solvent mixture having a boiling point of at least 40° C.

In some embodiments, at least a portion of oxygenated hydrocarbons produced in the hydrothermal hydrocatalytic reaction zone are recycled within the process and system to at least in part form the in situ generated solvent, which is used in the biomass digestion process. Further, by controlling the rate of digestion of biomass to lower molecular weight fragments in the hydrothermal hydrocatalytic reaction (e.g., hydrogenolysis process), hydrogenation reactions can be conducted along with the hydrogenolysis reaction at temperatures ranging of from 110° C., preferably from about 150° C. to less than 300° C., most preferably from about 240° C. to about 270° C. As a result the fuel forming potential of the biomass feedstock fed to the process can be increased.

In various embodiments, the fluid phase digestion medium (liquid digestive solvent) in which the hydrothermal digestion and catalytic reduction reaction (in the hydrothermal hydrocatalytic reaction zone) are conducted, may comprise an organic solvent and water. The liquid digestive solvent mixture may have a normal boiling point (i.e., at atmospheric pressure) of at least 40° C., preferably at least 60° C., more preferably at least 80° C. Although any organic solvent that contains some oxygen atoms may be used as a digestion solvent, particularly advantageous organic solvents are those that can be directly converted into fuel blends and other materials and hence do not require extensive separation from intermediate streams used in the production of biofuels, or co-product streams used as fuel or separated and processed as chemical products. That is, particularly advantageous organic solvents are those that may be co-processed along with the alcoholic or oxygenated components during downstream processing reactions into fuel blends and other materials. Suitable organic solvents in this regard may include, for example, ethanol, ethylene glycol, propylene glycol, glycerol, phenolics and any combination thereof. In situ generated organic solvents are particularly desirable in this regard.

In some embodiments, the liquid phase digestive solvent may comprise between about 1% water and about 99% water. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the liquid phase digestive solvent may comprise about 90% or less water by weight. In other embodiments, the fluid phase digestion medium may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

In some embodiments, catalysts capable of activating molecular hydrogen hydrothermal hydrocatalytic catalysts, which are capable of activating molecular hydrogen (e.g., hydrogenolysis catalyst) and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst may be deposited on a catalyst support that may not itself be catalytically active.

In some embodiments, the hydrothermal hydrocatalytic catalyst may comprise a slurry catalyst. In some embodiments, the slurry catalyst may comprise a poison-tolerant catalyst. As used herein the term "poison-tolerant catalyst" refers to a catalyst that is capable of activating molecular hydrogen without needing to be regenerated or replaced due to low catalytic activity for at least about 12 hours of continuous operation. Use of a poison-tolerant catalyst may be particularly desirable when reacting soluble carbohydrates derived from cellulosic biomass solids that have not had catalyst poisons removed therefrom. Catalysts that are not poison tolerant may also be used to achieve a similar result, but they may need to be regenerated or replaced more frequently than does a poison-tolerant catalyst.

In some embodiments, suitable poison-tolerant catalysts may include, for example, sulfided catalysts. In some or other embodiments, nitrided catalysts may be used as poison-tolerant catalysts. Sulfided catalysts suitable for activating molecular hydrogen and buffers suitable for use with such catalysts are described in commonly owned U.S. Patent Application Publication Nos. US2012/0317872, US2013/0109896, US2012/0317873, and US20140166221, each of which are incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise (a) sulfur and (b) Mo or W and (c) Co and/or Ni or mixtures thereof. The pH buffering agent, may be suitable be an inorganic salt, particularly alkali salts such as, for example, potassium hydroxide, sodium hydroxide, and potassium carbonate or ammonia. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be distributed in the cellulosic biomass solids using fluid flow. Illustrative techniques for catalyst sulfiding that may be used in conjunction with the methods described herein are described in U.S. Patent Application Publication No. US2010/0236988, and incorporated herein by reference in its entirety.

In various embodiments, slurry catalysts used in conjunction with the methods described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

In some embodiments, the catalysts used in conjunction with the processes described herein may be operable to generate molecular hydrogen. For example, in some embodiments, catalysts suitable for aqueous phase reforming (i.e., APR catalysts) may be used. Suitable APR catalysts may include, for example, catalysts comprising Pt, Pd, Ru, Ni, Co, or other Group VIII metals alloyed or modified with Re, Mo, Sn, or other metals such as described in United States Patent Publication No. US2008/0300435, and incorporated herein by reference in its entirety.

As described above, one or more liquid phases may be present when digesting cellulosic biomass solids. Particularly when cellulosic biomass solids are fed continuously or semi-continuously to the hydrothermal (hydrocatalytic) digestion unit, digestion of the cellulosic biomass solids may produce multiple liquid phases in the hydrothermal digestion unit. The liquid phases may be immiscible with one another, or they may be at least partially miscible with one another. In some embodiments, the one or more liquid phases may comprise a phenolics liquid phase comprising lignin or a product formed therefrom, an aqueous phase comprising the alcoholic component, a light organics phase, or any combination thereof. The alcoholic component being produced from the cellulosic biomass solids may be partitioned between the one or more liquid phases, or the alcoholic component may be located substantially in a single liquid phase. For example, the alcoholic component being produced from the cellulosic biomass solids may be located predominantly in an aqueous phase (e.g., an aqueous phase digestion solvent), although minor amounts of the alcoholic component may be partitioned to the phenolics liquid phase or a light organics phase. In various embodiments, the slurry catalyst may accumulate in the phenolics liquid phase as it forms, thereby complicating the return of the slurry catalyst to the cellulosic biomass solids in the manner described above. Alternative configurations for distributing slurry catalyst particulates in the cellulosic biomass solids when excessive catalyst accumulation in the phenolics liquid phase has occurred are described hereinafter.

Accumulation of the slurry catalyst in the phenolics liquid phase may, in some embodiments, be addressed by conveying this phase and the accumulated slurry catalyst therein to the same location where a fluid phase digestion medium is being contacted with cellulosic biomass solids. The fluid phase digestion medium and the phenolics liquid phase may be conveyed to the cellulosic biomass solids together or separately. Thusly, either the fluid phase digestion medium and/or the phenolics liquid phase may motively return the slurry catalyst back to the cellulosic biomass solids such that continued stabilization of soluble carbohydrates may take place. In some embodiments, at least a portion of the lignin in the phenolics liquid phase may be depolymerized before or while conveying the phenolics liquid phase for redistribution of the slurry catalyst. At least partial depolymerization of the lignin in the phenolics liquid phase may reduce the viscosity of this phase and make it easier to convey. Lignin depolymerization may take place chemically by hydrolyzing the lignin (e.g., with a base) or thermally by heating the lignin to a temperature of at least about 250° C. in the presence of molecular hydrogen and the slurry catalyst. Further details regarding lignin depolymerization and the use of viscosity monitoring as a means of process control are described in commonly owned U.S. Patent Application Publication No. US20140117275, which disclosure is incorporated herein by reference in its entirety.

In some embodiments, a phenolics liquid phase formed from the cellulosic biomass solids may be further processed. Processing of the phenolics liquid phase may facilitate the catalytic reduction reaction being performed to stabilize soluble carbohydrates. In addition, further processing of the phenolics liquid phase may be coupled with the production of glycols or dried monohydric alcohols for feeding to a condensation catalyst. Moreover, further processing of the phenolics liquid phase may produce methanol and phenolic compounds from degradation of the lignin present in the cellulosic biomass solids, thereby increasing the overall weight percentage of the cellulosic biomass solids that may be transformed into useful materials. Finally, further processing of the phenolics liquid phase may improve the lifetime of the slurry catalyst.

Various techniques for processing a phenolics liquid phase produced from cellulosic biomass solids are described in commonly owned U.S. Patent Application Publication Nos. US20140121419, US20140117277, which disclosures are incorporated herein by reference in its entirety. As described therein, in some embodiments, the viscosity of the phenolics liquid phase may be reduced in order to facilitate conveyance or handling of the phenolics liquid phase. As further described therein, deviscosification of the phenolics liquid phase may take place by chemically hydrolyzing the lignin and/or heating the phenolics liquid phase in the presence of molecular hydrogen (i.e., hydrotreating) to depolymerize at least a portion of the lignin present therein in the presence of accumulated slurry catalyst. Deviscosification of the phenolics liquid phase may take place before or after separation of the phenolics liquid phase from one or more of the other liquid phases present, and thermal deviscosification may be coupled to the reaction or series of reactions used to produce the alcoholic component from the cellulosic biomass solids. Moreover, after deviscosification of the phenolics liquid phase, the slurry catalyst may be removed therefrom. The catalyst may then be regenerated, returned to the cellulosic biomass solids, or any combination thereof.

In some embodiments, heating of the cellulosic biomass solids and the fluid phase digestion medium (liquid digestive solvent) to form soluble carbohydrates and a phenolics liquid phase may take place while the cellulosic biomass solids are in a pressurized state. As used herein, the term "pressurized state" refers to a pressure that is greater than atmospheric pressure (1 bar). Heating a fluid phase digestion medium in a pressurized state may allow the normal boiling point of the digestion solvent to be exceeded, thereby allowing the rate of hydrothermal digestion to be increased relative to lower temperature digestion processes. In some embodiments, heating the cellulosic biomass solids and the fluid phase digestion medium may take place at a pressure of at least about 30 bar. In some embodiments, heating the cellulosic biomass solids and the fluid phase digestion medium may take place at a pressure of at least about 60 bar, or at a pressure of at least about 90 bar. In some embodiments, heating the cellulosic biomass solids and the fluid phase digestion medium may take place at a pressure ranging between about 30 bar and about 430 bar. In some embodiments, heating the cellulosic biomass solids and the fluid phase digestion medium may take place at a pressure ranging between about 50 bar and about 330 bar, or at a pressure ranging between about 70 bar and about 130 bar, or at a pressure ranging between about 30 bar and about 130 bar. Reference herein to pressure(s) is to gauge pressure(s).

The digestion and hydrodeoxygenation of the biomass solid described above, produces a stable oxygenated hydrocarbon intermediate product, 12, that have a viscosity of less than 100 centipoise (at 50° C.), preferably less than 40 centipoise, a diol content (e.g., glycols) of at least 2 wt. %, preferably of at least 5 wt %, less than 2 wt % of sugar, and less than 2 wt % acid based on acetic acid equivalent, based on the total stream composition, and at least 60% of carbon exists in molecules having 9 carbon atoms or less. By the term "stable", the product is stable enough to be stored for at least 30 days where the viscosity does not change more than 50% and the main components (top 10 percent based on mass basis) does not change in concentration by more than 10%.

The stable oxygenated hydrocarbon intermediate product is separated into an organic phase 22 and an aqueous phase 24 in a liquid-liquid separation zone 20. An aromatics-rich higher hydrocarbon comprising toluene or an aliphatic-rich higher hydrocarbon boiling within the range of 40° C. to 210° C. (light alkylate) 77 may be added to the stable oxygenated hydrocarbon intermediate product to induce or enhance phase separation. Aliphatic-rich higher hydrocarbon boiling within the range of 40° C. to 210° C. may contain C5-C10 alkanes (branched or straight chain), such as pentane, hexane, heptane, octane, nonane, decane, or mixtures thereof. Such aromatics-rich higher hydrocarbon or aliphatic-rich higher hydrocarbon may optionally be provided via recycle of an aromatic-rich higher hydrocarbon product containing toluene from a process reaction product from the present process as described below or via recycle of an aliphatic-rich higher hydrocarbon from a process reaction product from the present process as described below.

The liquid-liquid separation of the aqueous phase and the organic phase can be by decanting, liquid-liquid extraction, centrifugation, or use of hydroclones or other devices using the density differences between immiscible phases as the basis for separation. By performing the liquid-liquid separation, multiple liquid phases are avoided in subsequent distillation 40 of the organic phase 22 and phenols can be separated from biofuels intermediates as a bottoms product 43. The phenols can optionally be recycled as solvent (not shown), optionally replacing use of toluene as extraction solvent, as phenols will form a phase immiscible with water at temperatures less than 200° C. temperatures used for digestion reaction. Optional phenol separation and recycle is performed by separate distillation (not shown) of the bottoms stream containing lignin asphalt. At least a portion of the organic phase may be recycled 47 as the extraction solvent and the organic remaining organic phase 42 (that contains less water and less diols) provided to the acid condensation zone 50 or 52.

The aqueous stream from liquid-liquid separation is rich in ethylene glycol (EG) and propylene glycol (PG) 24, which would form excessive coke if routed directly to condensation reaction zone 50, such as ZSM-5 acid condensation. Optionally, this stream 24 may be vaporized 25 to separate from salts and base (ash separation) 27, and passed over amorphous silica-alumina catalyst (ASA) in a diol conversion zone 30 to condense EG and PG to less reactive intermediates. This intermediates stream 32 can be passed over ZSM-5 catalyst under conditions to make aromatics rich higher hydrocarbons, with reduced coking and/or can be passed over solid acid condensation catalyst under conditions to make aliphatic-rich higher hydrocarbons in an acid condensation zones 50, 51 and 55. These acid condensation products 52, 57 can be further based washed for aromatics rich higher hydrocarbons or hydrotreated for aliphatic-rich higher hydrocarbons, in a further processing zone 70, 72, and 73, to produce aromatics rich liquid biofuel components or aliphatic-rich liquid biofuel components 75, 74.

For the diol conversion zone, it was found that contacting (and reacting) the aqueous phase containing diol with an acidic amorphous silica alumina catalyst, preferably mildly acidic amorphous silica alumina catalyst, at a temperature in the range of 300° C. to 400° C. producing monooxygenated stream prior to condensation reaction can reduce coke formation on the catalyst during subsequent condensation reaction. The aqueous phase maybe used directly or concentrated by vaporization and/or distillation and/or other means to a concentration of at least 5%, preferably at least 7%, preferably at least 10%, more preferably at least 12%, most preferably at least 15% by weight organics in the aqueous phase. It has been found that sufficient amount of organics is necessary in order for condensation or oligomerization reaction to preferably convert the diols and oxygenates to other than C2 and C3 hydrocarbons. Optionally, at least a portion of the condensation product from the aqueous phase maybe recycled to contact with the acidic amorphous silica alumina catalyst to increase the organics concentration.

In the inventive process, at least a portion of the aqueous phase is contacted, in a diol conversion zone, 30, with an acidic amorphous silica alumina catalyst at a temperature in the range from 300° C. to 400° C., preferably 325° C. to 375° C., thereby producing monooxygenate-containing stream, 32, containing water, monooxygenates and unsaturated aliphatic hydrocarbons having a normal boiling point of at least 40° C. The temperature and pressure is at a range that optimizes diol conversion while minimizing coke formation (by oligomerization or condensation reactions). The reaction typically converts at least 25%, preferably at least 50%, most preferably at least 75% of diols initially present. Typically, the weight hourly space velocity is in the range of 0.2 to 5 for the monooxygenate formation step.

The acidic amorphous silica-alumina catalyst is a solid catalyst that may be prepared in a number of ways which are known in the art. For example, by precipitating alumina in a silica slurry, followed by firing. Some other examples include precipitation of hydrous alumina onto amorphous silica hydrogel, reacting a silica sol with an alumina sol, coprecipitation from sodium silicate/aluminum salt solution. The sulfate and the sodium, which may be introduced with the alumina precursors and sulfuric acid, may be removed by washing. The resulting silica alumina material can be shaped in various shapes, for example, by extruding, oil drop process, or pressing. To produce the acidic amorphous silica-alumina catalyst, the material is dried and calcined. The BET surface area of the catalyst is typically greater than 200 m$^2$/g, preferably in the range of 300 m$^2$/g to 500 m$^2$/g. The total pore volume is typically in the range of 0.7 to 1.0 cc/g measured using water method. Although described herein as amorphous, the silica alumina materials useful in embodiments described herein may contain a minor amount of crystalline alumina and/or aluminosilicate, depending on the source of the alumina material used to prepare the precipitated alumina-silica precursor, the amount of the alumina in the alumina-silica, as well as the calcination temperature. The ratio of silica to alumina may vary between 1:99 to 99:1, preferably 15:85 to 96:4. In some embodiment, 15:85 to 65:35, preferably 15:85 to 30:70 for low silica content solid amorphous silica-alumina catalyst, preferably 35:65 to 55:45 for higher silica solid amorphous silica-alumina catalyst. In another embodiment, milder acidity amorphous silica to alumina catalyst, the ratio of silica to alumina may vary between 45:55 to 96:4, more preferably 45:55 to 90:10. Solid acid amorphous silica-alumina catalyst is available commercially, for example, from Criterion Catalyst Co., such as X-600 catalyst series, X-503 catalyst, X-801 catalyst or from CRI Catalyst Co. such as KL-7122 catalyst.

As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. The term "condensation catalyst" will refer to a catalyst that facilitates, causes or accelerates such chemical transformation.

Distillation may also be used for a process where the digestion and hydrodeoxygenation step has been optimized to produce mainly diols and higher molecular weight monooxygenates, such that water with only a small amount of monooxygenates less than C4 are present as the aqueous miscible component.

At least a (second) portion of the organic phase 42 containing the monooxygenates or the monooxygenate-containing stream 32 having boiling point of at least 40° C. is contacted with a solid acid condensation catalyst separately, for example s shown in FIG. 3 or to the same catalyst, for example, as shown in FIG. 1 or 2, at a temperature in the range from 275° C. to about 425° C. producing a higher hydrocarbons stream in a condensation reaction zone, 51 and 55 in FIG. 3 and 50 in FIG. 1 and FIG. 2.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons. In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure. Suitable condensation catalysts include, for example, acid condensation catalysts described in US20140275515 which disclosure is hereby incorporated by reference.

The condensation products 52 may be aromatics-rich hydrocarbon stream when a shape selective condensation catalyst, such as zeolitic catalyst, particularly ZSM-5 catalyst, is used in the condensation reaction. To produce aromatics-rich hydrocarbon stream, the acidic ZSM-5 catalyst is contacted at a temperature in the range from 325° C. to about 425° C., preferably 350° C. to 400° C., in the condensation reaction zone, The temperature and pressure is at a range that optimizes condensation reaction while minimizing coke formation. The pressure range may be from ambient pressure (atmospheric) to slight partial pressure, for example, total pressure of up to about 200 psi. The aromatics rich hydrocarbon stream can optionally be washed with aqueous base such as sodium hydroxide, potassium hydroxide to remove residual acids and phenolics (washing zone, 70) to produce biofuel useful as gasoline, 75. These aqueous base typically have a pH of at least 9. The aromatics-rich higher hydrocarbons stream may have at least 50 wt % of aromatics containing hydrocarbon based on the aromatics-rich hydrocarbons stream. The entire organic phase can also be sent to the condensation step. The yield may be greater than 40% of carbons based on biomass carbons due to the increase catalyst uptime (amount of monooxygenated stream passed over the condensation catalyst). Aromatics as defined herein can be quantified by GC-MS analysis and includes any aromatic containing hydrocarbon that contains aromatic rings that are not oxygenated, such as mesitylene, based on molecular content.

The condensation product 52, may be low aromatics, paraffinics-containing stream (aliphatic-rich higher hydrocarbons) when other than shape selective condensation catalyst described above is used in the condensation reaction. The low aromatics, paraffinic-containing stream may further treated in a hydrotreating step (hydrotreating zone, 70) to produce biofuel useful as diesel, 75. This step can be any conventional hydrotreating process. This includes fixed or ebulated bed operations at conventional operating conditions such as temperatures in the range of 250° C. to 450° C., preferably 300° C. to 380° C. Pressures are also conventional such as 20-70 bar of hydrogen. Catalysts used in the hydrotreating step are preferably those employed conventionally, such as mixed cobalt and/or nickel and molybdenum sulfides supported on alumina and mixed nickel and tungsten sulfides supported on alumina or silica. The combined process of this invention will also benefit newly developed catalysts such as those containing ruthenium sulfide and catalysts using novel supports such as silica-aluminas, carbons or other materials. For details on the state of the art in conventional hydrotreating processes, we refer to "Hydrotreating Catalysis-Science and Technology", by H. Topsøe, B. S. Clausen and F. E. Massoth, Springer-Verlag Publishers, Heidelberg, 1996.

For FIG. 3, at least a (second) portion of the organic phase 42 containing the monooxygenates may be contacted with a solid acid condensation catalyst under conditions effective to produce low aromatics, paraffinics-containing stream 52 in acid condensation zone 51 to produce an aliphatics and the monooxygenate-containing stream 32 may be contacted with a ZSM-5 catalyst under conditions effective to produce aromatics-rich hydrocarbons stream 57 in acid condensation zone 55, The aromatics-rich hydrocarbons stream 57 may be base washed in further processing zone 73 and the aliphatic-rich higher hydrocarbons 52 may be hydrotreated in further processing zone 72.

It has been found that ASA catalyst react EG and PG (enriched in the aqueous extract) to intermediates which retain some oxygenate functionality and can be converted to liquid biofuels, yet will not lead to excessive coke formation.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction To facilitate a better understanding of the present invention, the following examples of preferred embodiments are given. In no way should the following examples be read to limit, or to define, the scope of the invention.

ILLUSTRATIVE EXAMPLES

Example 1: Digestion and Hydrodeoxygenation of Lignocellulosic Biomass

To screen for reaction selectivity in digestion of biomass, a 50-milliliter Parr 4590 reactor was charged with 6.01 grams of tetrahydrofuran and 17.99 grams of deionized water solvent, together with 0.099 grams of potassium hydroxide, and 0.1075 grams of Raney™ cobalt catalyst (from WR Grace 2724).

The reactor was then charged with 1.99 grams of southern pine mini-chips (10% moisture), of nominal size 3×5×5 mm in dimension, before pressuring with 52 bar of hydrogen, and heating with stirring to 190° C. for 1 hour, followed by heating to 240° C. for 4 hours. At the end of the 5-hour reaction cycle, the reactor was cooled, and allowed to gravity settle overnight.

The reaction cycle was repeated three times via addition of 2 more grams of wood chips, and re-pressuring with 52 bar of $H_2$ before heating using the same temperature profile.

After four cycles, the reactor product was analyzed by gas chromatography using a 60-m×0.32 mm ID DB-5 column of 1 micrometer thickness, with 50:1 split ratio, 2 ml/min helium flow, and column oven at 40° C. for 8 minutes, followed by ramp to 285° C. at 10° C./min, and a hold time of 53.5 minutes. The injector temperature was set at 250° C., and the detector temperature was set at 300° C. A range of alkanes, ketone and aldehyde monooxygenates as well as glycol intermediates including ethylene glycol (EG), 1,2-propylene glycol (PG) and glycerol were observed. Total products observed in the gas chromatographic analysis summed to about 30% of the maximum expected yield if all carbohydrates were converted to mono-oxygenated or diol products. Ethylene glycol (EG) formation and 1,2-propylene glycol (PG) formation comprised approximately 20% of observed products. All observed reaction products exhibited volatility greater than C6 sugar alcohol sorbitol.

Examples 2 and 3: Digestion and Hydrodeoxygenation of Lignocellulosic Biomass

Example 1 was repeated with use of 0.3083 (Example 2) and 0.4051 (Example 3) grams of Raney Cobalt catalyst. For example 2, the amount of ethylene glycol formed increased to 1.49 weight percent, and 1,2-propylene glycol formation increased to 1.65 weight percent. Total GC observable products increased to 10.5 wt. %, or 96% of the expected product formation from selective conversion of carbohydrates present in wood feed. Glycols EG and PG comprised about 29% of observed products.

For example 3 with 0.4051 grams of Raney Cobalt catalyst, 1.4 wt. % ethylene glycol was formed, together with 1.64 wt. % of 1,2-propylene glycol. Observed yields were estimated as 99% of those expected from complete conversion of carbohydrates in wood feed, while ethylene glycol and 1,2-propylene glycol comprised about 28% of observed products.

These examples show formation of diols ethylene glycol and 1,2-propylene glycol via simultaneous digestion and hydrotreating reaction of woody biomass, in the presence of hydrogen and a metal catalyst capable of activating molecular hydrogen. The diols were the largest single components observed in gas chromatographic analysis of product. Yields were increased by increasing the catalyst concentration, to increase the rate of hydrotreating and stabilization of intermediates derived from the hydrothermal digestion of woody biomass.

Example 4: Digestion and Hydrodeoxygenation of Lignocellulosic Biomass

A 75-ml Parr5000 reactor was charged with 6.04 grams of 2,6-dimethyl phenol (xylenol), 18.06 grams of deionized water, 0.207 grams of a mixture of 860 ppm dimethylsulfoxide in deionized water, 0.085 grams of potassium hydroxide buffer, and 0.45 grams of nickel-oxide promoted cobalt molybdate catalyst (DC-2534, containing 1-10% cobalt oxide and molybdenum trioxide (up to 30 wt. %) on alumina, and less than 2% nickel), obtained from Criterion Catalyst & Technologies L.P., and sulfided by the method described in US2010/0236988 Example 5.

The reactor was then charged with 2.07 grams of southern pine mini-chips (10% moisture), of nominal size 3×5×5 mm in dimension, before pressuring with 40 bar of hydrogen, and heating to 200° C. for 1 hours, then ramping to 255° C. for 1.5 hours.

GC analysis of final liquid revealed 1.63 wt. % ethylene glycol and 1.60 wt. % propylene glycol, for a yield of more than 30% of the GC-measured products derived from carbohydrates.

Example 5: Sulfided Cobalt Molybdate Catalyst at Higher Temperature

Example 4 was repeated with a heating cycle of 1 hour at 200° C. followed by 1.5 hours at 265° C. Observed ethylene glycol and propylene glycol produced was 1.01 and 1.08 wt. % respectively, with the higher temperature end condition.

Examples 6 & 7

Digestion and Hydrodeoxygenation of Lignocellulosic Biomass

For Example 6, the experiment of Example 4 was repeated with a solvent mixture of 12.5% cresol in deionized water, and a heating cycle of 1 hour at 190° C. followed by 4 hours at 240° C. GC analysis indicated a yield of ethylene glycol (EG) and 1,2-propylene glycol (PG) corresponding to 6.75% of total carbohydrates charged, with ethylene glycol comprising 36% of these total of these diols. Wood digestion was complete, and more than 100 components with retention time less than sorbitol were detected in the GC analysis.

For Example 7, the experiment of Example 6 was repeated with addition of 1.8 grams of 99% purity cellulosic floc, instead of pine wood. Yield of EG and PG was calculated as 8.5% of the total carbohydrate charged.

Examples 8 & 9: Digestion and Hydrodeoxygenation of Lignocellulosic Biomass

Experiment 6 was repeated with use of 0.251 grams of 5% Platinum/alumina as catalyst (STREM Chemicals). The reactor was again heated for 1 hour at 190° C. followed by 4 hours at 240° C. Yield of diols EG and PG was 4.78% of the carbohydrate charged to the reactor.

Experiment 7 was repeated with 0.248 grams of the 5% Pt/alumina catalyst as reaction catalyst. Yields of diols EG and PG were calculated as 5.26% of the total carbohydrate charged to the reactor as cellulosic floc.

Experiments 6-9 conducted under otherwise identical conditions, show substantial formation of diols as products, among a large number of components formed with boiling points less than sorbitol. Yields of diols EG and PG were higher with the sulfided cobalt molybdate catalyst, than for the supported platinum catalyst, under the conditions tested.

Example 10: Generation of Digestion and Hydrodeoxygenation Intermediate

A 2-Liter Parr reactor with was charged with 1000.5 grams of deionized water solvent, 0.401 grams of potassium hydroxide buffer, and 29.8 grams of Raney Cobalt 2724 catalyst (WR Grace). 66.7 grams of southern pine wood at nominal 10% moisture were added for reaction cycles conducted under 52 bar of $H_2$, with heating to 160° C. for 1 hour, followed by 190° C. for 1 hour, followed by 240° C. for 3 hours.

Six cycles of wood addition were completed, with KOH buffer added at 1.5-2.0 grams per cycle, to maintain pH greater than 4.5. After 6 cycles, 250 grams of toluene were added (Sigma-Aldrich HPLC grade), and the reactor was stirred for one hour at 150° C. to extract. Stirring was stopped, the reactor was cooled, vented, and opened for removal of liquid phases.

44.2 grams of organic upper layer, and 1019 grams of aqueous lower layer were decanted via suction. The remaining wood residue and catalyst were dissolved in 250 grams of acetone solvent, for analysis by gas chromatography.

A sample of the aqueous layer product was analyzed by gas chromatography using a 60-m×0.32 mm ID DB-5 column of 1 µm thickness, with 50:1 split ratio, 2 ml/min helium flow, and column oven at 40° C. for 8 minutes, followed by ramp to 285° C. at 10° C./min, and a hold time of 53.5 minutes. The injector temperature was set at 250° C., and the detector temperature was set at 300° C. Gas Chromatographic—Mass Spec (GCMS) was effected using the same protocol.

Principal products were ethylene glycol, 1,2-proplene glycol, along with light monooxygenates C1-C3, intermediate C4-C6 monooxygenates (ketones, alcohols) and diols. Several phenolic components were formed (methoxypropylphenol, propylphenol) and extracted via toluene into the upper organic layer.

771.6 grams of the aqueous intermediate product from above and 8.1 grams of ceramic boiling chips were charged to a 2-liter 24/40 3-neck flask equipped with a short path Vigreux column (approximately 4 stages). The flask was brought to a boil under a nominal atmosphere of nitrogen, and 702.5 grams of a water-rich cut were removed. Vacuum was applied (approximately 50-100 Torr), and 77.9 grams of a middle boiling cut were removed as the bottoms kettle temperature was ramped from 100 to 350° C. Maximum tops temperature was 150° C. A bottoms residue of 13.1 grams was obtained, for a mass balance closure of 98.8%.

The middle boiling second distillate fraction was analyzed by GC-mass spec, to reveal the composition shown in Table 1 below. A large number of diol intermediates were formed.

Comparative Example A

Ni was impregnated on ZSM-5 (CBV2314 having SAR of 23 from Zeolyst International). 50 g of ZSM-5 ⅛ inch extrudate was impregnated with Ni(NO₃)₂.6H₂O (2.48 g) dissolved in deionized water (13.76 g) by insipient wetness. After all the liquid had been adsorbed, the extrudate was dried for 1 hr at 125° C., then calcined for 3 hrs. at 400° C.

A model feed mixture was prepared with PG/EG/water (wt. % 45%/5%/50) and charged to a ½ OD continuous flow reactor containing 13.24 g of the Ni impregnated ZSM-5, 7 bar hydrogen flowing at 50 cc/min. WHSV 1.22 total feed, 0.6 on organic basis. The catalyst needed to be regenerated due to loss of activity from coking. Reaction ran for 1 day at which point catalyst was making only traces of product. Coke burn restored activity, but activity was completely lost again after 2nd sample (1 day).

Example 11

A model feed mixture representing a diol conversion product mixture (i.e., after contact with amorphous silica alumina) was prepared with IPA/THF/acetone/acetic acid/1,3 PDO/water (wt. % 15/7/4/3/1/70) and charged to a ½ inch OD continuous flow reactor containing 13.4 g Ni impregnated ZSM-5 (SAR23) prepared as above, at 375° C., 7 bar hydrogen flowing at 50 cc/min WHSV 1.0 total feed, 0.3 on organic basis. The catalyst needed to be regenerated due to loss of activity from coking. Coke burns were carried out once/week. Product from this reaction was 15% organic phase. As can be seen above, by feeding a lower diol content feed representing diol conversion-treated feed compared to directly feeding diols to ZSM-5 condensation reaction in Comparative Example A, the activity between coke burns was extended from daily to once a week.

Example 12

Feed from Example 10, (fraction 2) was diluted 1/1 with DI water 7.5 g of ASA X600 (amorphous silica alumina trilobe extrudate from Criterion Catalyst Co., LP, 55% alumina (Al₂O₃), 45% silica (SiO₂)) was charged to a 10 inch reactor and heated to 350° C. under flowing nitrogen (50 cc/min, 130 psig reactor pressure). Feed was introduced at 7.2 g/hr. 85 g of liquid product was collected of which 7 g was organic phase while the remainder comprised an aqueous phase.

Example 13

Both phases from Example 12 were recombined and a portion fed over 7.5 g of ZSM-5 (CBV2314 Zeolite from Zeolyst International) at a rate of 14 g/hr. 65 g of product was collected, 2.6 g of organic phase and the remainder an aqueous phase.

A table of compiled GCMS data from Examples 10, 12 and 13 above is provided below. Other is C5-C6 higher oxygenates such as triols etc.).

TABLE 1

| digestion liquor | | | | | |
|---|---|---|---|---|---|
| mono-ol | diol | ketone | cyclic ether | lactone | other |
| 9.62 | 48.52 | 3.69 | 3.73 | 3.11 | 31.33 |

| ASA product | | | | | |
|---|---|---|---|---|---|
| olefin | diene | cyclic ether | ketones | aldehyde | aromatic |
| 17.70 | 9.49 | 20.42 | 19.20 | 19.28 | 14.59 |

TABLE 1-continued

| ZSM5 product | | | | | |
|---|---|---|---|---|---|
| mono-ox | alkanes | aromatics | indanes | naphthalenes | acid |
| 8.07 | 1.39 | 75.09 | 6.47 | 8.04 | 3.15 |

As can be seen from the table above, diols were below detection limit after diol conversion reaction with ASA.

The invention claimed is:

1. A process for the production of a higher hydrocarbon from solid biomass, said process comprising:
   a. providing a biomass solid containing cellulose, hemicellulose, and lignin;
   b. digesting and hydrodeoxygenating the biomass solid in a liquid digestive solvent in the presence of a hydrothermal hydrocatalytic catalyst and hydrogen at a temperature in a range of 110° C. to less than 300° C. and at a pressure in a range of from 20 bar to 200 bar, said liquid digestive solvent containing a solvent mixture having a boiling point of at least 40° C., to form a stable oxygenated hydrocarbon intermediate product having a viscosity of less than 100 centipoise (at 50° C.), a diol content of at least 2 wt. %, less than 2 wt. % of sugar, and less than 2 wt. % acid (based on acetic acid equivalent), based on the stable oxygenated hydrocarbon intermediate product, and at least 60% of carbon in the stable oxygenated hydrocarbon intermediate product exists in molecules having 9 carbon atoms or less;
   c. separating the stable oxygenated hydrocarbon intermediate product to an organic rich phase and an aqueous rich phase;
   d. reacting at least a portion of the aqueous rich phase with an acidic amorphous silica alumina catalyst at a temperature in a range from 300° C. to 400° C. to convert diol in the aqueous rich phase into monooxygenate compounds thereby producing monooxygenate-containing stream comprising water, organic monooxygenates, and unsaturated aliphatic hydrocarbons;
   e. contacting at least a portion of the monooxygenate-containing stream with a solid acid condensation catalyst at a temperature in a range from 275° C. to about 425° C. thereby producing a first higher hydrocarbons stream; and
   f. contacting at least a portion of the organic rich phase with a solid acid condensation catalyst at a temperature in a range from 275° C. to about 425° C. thereby producing a second higher hydrocarbons stream.

2. The process of claim 1 wherein the monooxygenate-containing stream and the organic rich phase are contacted with the same solid acid condensation catalyst.

3. The process of claim 1 wherein at least one of the solid acid condensation catalyst is ZSM-5.

4. The process of claim 1 wherein at least one of the solid acid condensation catalyst is selected from the group consisting of mineral based acidic catalyst and acidic zeolites.

5. The process of claim 3 wherein the step f produces an aromatics-rich higher hydrocarbons stream having at least 50 wt % of aromatics containing hydrocarbon including toluene based on the aromatics-rich higher hydrocarbons stream.

6. The process of claim 5 wherein the aromatics-rich higher hydrocarbons stream comprising toluene is added to the stable oxygenated hydrocarbon intermediate product prior to the step c.

7. The process of claim 6 wherein the aromatics-rich higher hydrocarbons stream is separated to an aromatics-enriched higher hydrocarbon stream by distillation prior to the addition.

8. The process of claim 1 wherein an aromatics-rich higher hydrocarbons stream comprising toluene is added to the stable oxygenated hydrocarbon intermediate product prior to separation in the step c.

9. The process of claim 8 wherein at least a portion of an organic rich phase containing aromatic hydrocarbons is provided to the stable oxygenated hydrocarbon intermediate product prior to separation in the step c.

10. The process of claim 1 wherein an aliphatic-rich higher hydrocarbon boiling within the range of 40° C. to 210° C. is added to the stable oxygenated hydrocarbon intermediate product prior to separation in the step c.

11. The process of claim 8 wherein at least a portion of an organic rich phase containing aliphatic-rich higher hydrocarbons boiling within a range of 40° C. to 210° C. is provided to the stable oxygenated hydrocarbon intermediate product prior to separation in the step c.

12. The process of claim 1 wherein the step b is carried out at a temperature in a range of 150° C. to 300° C.

13. The process of claim 1 wherein the acidic amorphous silica alumina catalyst has a BET surface area of greater than 200 m$^2$/g.

14. The process of claim 1 wherein the hydrothermal hydrocatalytic catalyst is a heterogeneous catalyst.

15. The process of claim 1 wherein the biomass solid is a lignocellulosic biomass.

16. The process of claim 1 wherein a fraction of diol converted in the step d is at least 25%.

17. The process of claim 1 wherein the solid acid condensation catalyst in the step f is selected from the group consisting of mineral based acidic catalyst and acidic zeolites and the solid acid condensation catalyst in the step e is ZSM-5.

18. The process of claim 17 wherein the first higher hydrocarbons stream from the reaction product of the step e is further processed to make gasoline fuel components and the second higher hydrocarbons stream from the reaction product of the step f is further processed to make diesel fuel components.

19. A process for the production of a higher hydrocarbon from solid biomass, said process comprising:
   a. providing a biomass solid containing cellulose, hemi-cellulose, and lignin;
   b. digesting and hydrodeoxygenating the biomass solid in a liquid digestive solvent in the presence of a hydrothermal hydrocatalytic catalyst and hydrogen at a temperature in a range of 110° C. to less than 300° C. and at a pressure in a range of from 20 bar to 200 bar, said liquid digestive solvent containing a solvent mixture having a boiling point of at least 40° C., to form a stable oxygenated hydrocarbon intermediate product having a viscosity of less than 100 centipoise (at 50° C.), a diol content of at least 2 wt. %, less than 2 wt. % of sugar, and less than 2 wt. % acid (based on acetic acid equivalent), based on the stable oxygenated hydrocarbon intermediate product, and at least 60% of carbon exists in molecules having 9 carbon atoms or less;
   c1. adding an aromatics-rich higher hydrocarbons comprising toluene to the stable oxygenated hydrocarbon intermediate product thereby providing a toluene-added stable oxygenated hydrocarbon intermediate;
   c2. separating the toluene-added stable oxygenated hydrocarbon intermediate to an organic rich phase and an aqueous rich phase;
   d. reacting at least a portion of the aqueous rich phase with an acidic amorphous silica alumina catalyst at a temperature in a range from 300° C. to 400° C. to convert diol in the aqueous rich phase into monooxygenate compounds thereby producing monooxygenate-containing stream containing water and organic monooxygenates;
   e. contacting at least a portion of the monooxygenate-containing stream with an acidic ZSM-5 catalyst at a temperature in a range from 325° C. to about 425° C. thereby producing water and an aromatics-rich higher hydrocarbons stream comprising toluene;
   f. contacting at least a portion of the organic rich phase with solid acid condensation catalyst at a temperature in a range from 275° C. to about 425° C. thereby producing a higher hydrocarbons stream; and
   g. recycling at least a portion of the aromatics-rich higher hydrocarbons stream comprising toluene obtained in the step e to the step c1 as a portion of the aromatics-rich higher hydrocarbons.

20. The process of claim 19 wherein the at least a portion of the monooxygenate-containing stream and the at least a portion of the organic rich phase are contacted with the same solid acid condensation catalyst.

21. The process of claim 19 wherein the step e and the step f are conducted in the same reactor.

22. The process of claim 19 wherein at least a portion of the organic rich phase is provided to the step c1 as a portion of the aromatics-rich higher hydrocarbons.

23. The process of claim 19 wherein the aromatics-rich higher hydrocarbons stream obtained in the step e is separated to an aromatics-enriched higher hydrocarbon stream by distillation prior to the addition in the step c1.

24. The process of claim 19 wherein the acidic amorphous silica alumina catalyst has a BET surface area of greater than 200 m$^2$/g.

* * * * *